(12) United States Patent
Marshall

(10) Patent No.: US 6,228,605 B1
(45) Date of Patent: *May 8, 2001

(54) DETECTION OF HELICOBACTER PYLORI IN THE STOMACH

(76) Inventor: Barry J. Marshall, 940 Stanley Dr., Earlysville, VA (US) 22936

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/832,332

(22) Filed: Mar. 26, 1997

Related U.S. Application Data

(63) Continuation of application No. 08/489,816, filed on Jun. 13, 1995, now abandoned, which is a continuation-in-part of application No. 08/142,600, filed on Oct. 28, 1993, now abandoned.

(30) Foreign Application Priority Data

Jun. 16, 1994 (DE) .................................. 44 20 936

(51) Int. Cl.[7] ...................................... C12Q 1/04
(52) U.S. Cl. .............................. 435/34; 435/12
(58) Field of Search ............... 435/12, 34, 288; 424/451, 453, 458, 474, 490; 436/169, 811

(56) References Cited

U.S. PATENT DOCUMENTS

| | | | |
|---|---|---|---|
| 3,121,041 | * | 2/1964 | Stern et al. .................. 167/51 |
| 3,383,283 | * | 5/1968 | Brindamour .................. 167/83 |
| 3,873,269 | * | 3/1975 | Kraffczyk .................... 23/230 B |
| 4,748,113 | * | 5/1988 | Marshall ...................... 435/12 |
| 4,830,010 | * | 5/1989 | Marshall ...................... 128/630 |
| 5,262,156 | * | 11/1993 | Alemohammad ............. 424/92 |
| 5,314,804 | * | 5/1994 | Boguslaski et al. .......... 435/12 |
| 5,439,801 | * | 8/1995 | Jackson ........................ 435/12 |
| 5,498,528 | * | 3/1996 | King ............................. 435/34 |
| 5,989,840 | * | 11/1999 | D'Angelo et al. ............ 435/7.32 |

* cited by examiner

Primary Examiner—Ralph Gitomer
(74) Attorney, Agent, or Firm—Sheldon H. Parker

(57) ABSTRACT

A method for the in vivo detection of urease-producing Helicobacter in the upper stomach is disclosed. The dense carrier is divided into two separate groups which are combined with separate reagent indicators, one of which also contains urea. The carriers are food soluble products, preferably sugar beads having a diameter of approximately 0.2 to 3.0 mm. The treated carriers and urea are encapsulated in a soluble capsule which is administered to a patient. The density of the carriers cause the capsule to migrate to the gastric mucosa, where the capsule, but not the reagents, is dissolved, placing the reagents and urea in direct contact with the gastric mucosa. The urea reacts with any urease present in the stomach by creating ammonia, which increases the pH in the immediate vicinity of the urea containing carrier and indicator beads. The two reagents react differently, through color change, to the increase in pH, which is viewed through use of an endoscope. A preferred first reagent is bromothymol blue (dibromothymolsulfonphthalein), which changes yellow in the presence of urease, and a preferred second reagent is phenol red (phenolsulfonphthalein), which turns red in the presence of urease.

15 Claims, 1 Drawing Sheet

DETECTION OF HELICOBACTER PYLORI IN THE STOMACH

This application is a continuation of Ser. No. 08/489,816 filed Jun. 13, 1995, now abandoned, which is a continuation in part of Ser. No. 08/142,600 filed Oct. 28, 1993, now abandoned, which claims priority to German application 44 20 936.3 filed Jun. 16, 1994.

BACKGROUND OF THE INVENTION

1. Brief Description of the Invention

The instant invention relates to a novel method of in vivo diagnosis of upper gastrointestinal diseases.

2. Brief Description of the Prior Art

Factors adversely affecting the function of the gastrointestinal system in humans are exceedingly varied in their nature. Such disorders may arise in the upper or lower gastrointestinal tracts, or both. There is a broad range of causes of gastrointestinal disorders, including genetic, physiological, environmental and psychogenic factors. Accordingly, the diagnosis and management of these disorders can be exceptionally difficult.

Among the chronic disorders of the upper gastrointestinal tract are those which fall under the general categories of gastritis and peptic ulcer disease. The upper gastrointestinal tract is generally defined as including the esophagus, the stomach, the duodenum, the jejunum and ileum. Peptic ulcers are lesions of the gastrointestinal tract lining, characterized by loss of tissue due to the action of digestive acids and pepsin. It has generally been held that peptic ulcers are caused by gastric hypersecretion, decreased resistance of the gastric lining to digestive acids and pepsin, or both. Gastritis is, by definition, an inflammation of the stomach mucosa. In practice, though, the disorder is manifested by a broad range of poorly-defined, and heretofore inadequately treated, symptoms such as indigestion, "heart burn", dyspepsia, and excessive eructation.

As with the management of any disorder, the rapid, precise, and accurate diagnosis of gastrointestinal disorders is of paramount importance. The typical means used to diagnose the gastrointestinal disorder presented by a given patient will depend upon such factors as the nature and severity of symptoms, the overall health of the individual, the medical history of the patient, the need for a specific diagnosis in order to implement a treatment with reasonable likelihood of success, and the availability of diagnostic devices. However, the diagnostic methods typically employed in the art are often slow, cumbersome, costly, and may yield equivocal or inaccurate results. Thus, for patients not having severe symptoms, a precise diagnosis of a gastrointestinal disorder might not be attempted. Such patients may simply be treated with conventional therapies, such as with antacids or drugs which inhibit stomach acid secretion. While such therapies might provide temporary symptomatic relief, a cure is often not effected. More effective treatments may depend upon better diagnoses of the actual underlying gastrointestinal disorder. In particular, it has been discovered that many such gastrointestinal disorders are mediated by infection of gastric mucosa by *Helicobacter pylori*. *H. pylori* is a Gram-negative spiral organism which produces the enzyme urease. The organism is predominantly found beneath the mucus layer of the luminal aspect of the gastric epithelium and in the gastric pits. Helicobacter can be diagnosed by blood test for antibodies, breath test, or biopsy of the stomach lining. Antibodies, however, can remain positive for many months after the bacteria have been eradicated. The presence of antibodies presents a falsely positive result in approximately 10 to 15% of patients. Biopsies are relatively quick; however, they add time, expense and risk. Although relatively minor, there is a 1 in 20,000 risk of bleeding from a biopsy site. Biopsies cannot be performed on patients who have a tendency to bleed, such as patients with hemophilia and liver disease. Additionally, it has recently been found that Helicobacter is patchy, thereby requiring multiple biopsies to obtain 100% accuracy. The cost for a biopsy is approximately $100. Biopsies also increase the risk of the person handling the tissue being exposed to HIV. If a urease test is used, the biopsy sample must be placed in the test by the nurse, thereby requiring an additional person during the test.

The prior art has disclosed testing for gastrointestinal disorders, the majority of which have been in vitro. Many tests have also been disclosed using urea and indicators.

Marshall, 4,748,113 discloses compositions and methods for the diagnosis of gastrointestinal disorders involving urease. Methods include obtaining a gastric sample material and contacting the material with a composition including urease and an indicator.

Marshall 4,830,010, discloses methods for the diagnosis of gastrointestinal disorders. The method steps include administration of urea-containing compositions prior to assay.

Steward et al, 5,139,934 disclose substrate compositions and method of urease assay. The method is an in vitro immunoassay that includes the use of pH indicators.

Nagatsu et al, 4,147,692 disclose methods and compositions for measuring enzymatic activities and correlating such activities with various disease states.

Kraffczyk et al, 3,873,369 disclose calorimetric indicators for the determination of urea.

Vasquez et al, 4,851,209 disclose in vivo diagnostic procedures for the clinical evaluation of gastrointestinal ulcer disease using radioactive isotopes. Procedures involve prior administration of a diagnostic pharmaceutical followed by scintigraphic imaging of the gastrointestinal area of interest with scintigraphic imaging equipment.

Although the use of urease or other indicators has been used in combination with pH indicators, all except Vasquez et al are conducted in vitro.

The instant invention discloses a method of detecting the alkaline pH change in vivo. The test dramatically cuts down the number of biopsies required and is safe for patients having any bleeding tendencies while being rapid and low cost. Additionally, through the color change, it can be determined if the change is a true positive or a false positive reaction.

BRIEF DESCRIPTION OF THE DRAWINGS

The advantages of the instant disclosure will become more apparent when read with the specification and the drawings, wherein.

SUMMARY OF THE INVENTION

Figure 1:
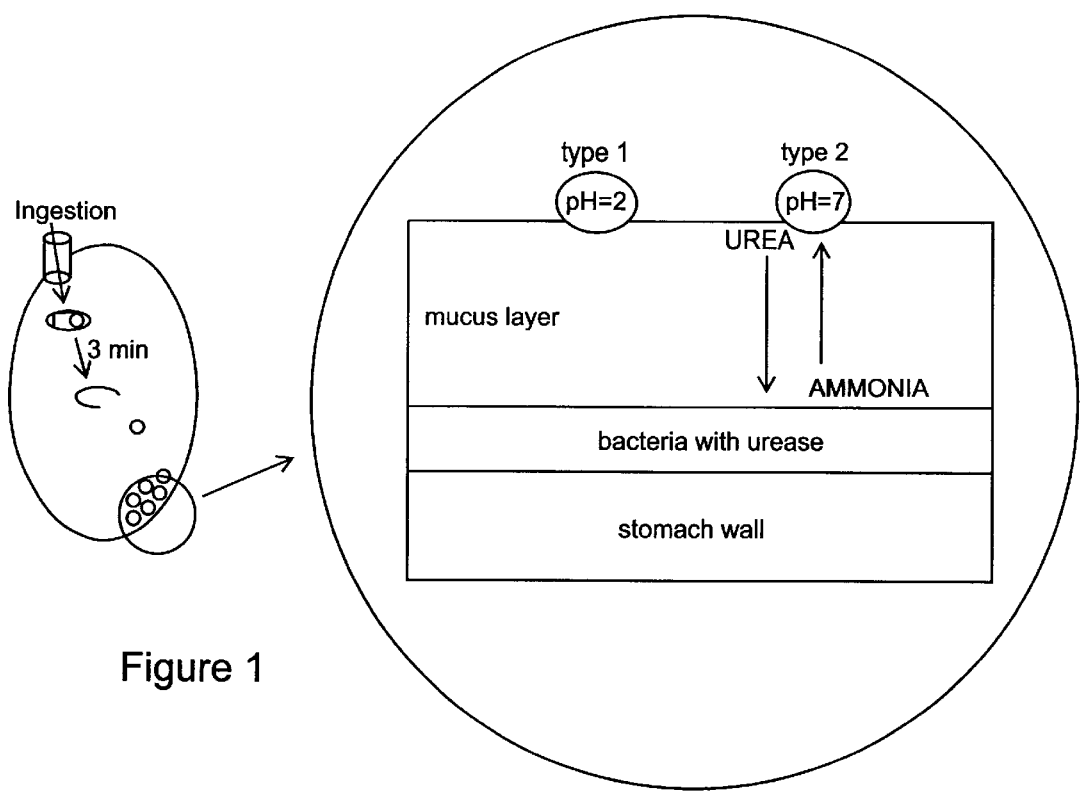
FIG. 1 illustrates the location of the beads in the stomach and the urea/ammonia transfer.

A method for the in vivo detection of urease-producing Helicobacter in the upper stomach is disclosed. A dense carrier is used which is divided into two separate groups, the first combined with a first reagent indicator and the second combined with a second reagent indicator and urea. The carriers are food soluble products, preferably sugar beads having a diameter of approximately 0.2 to 3.0 mm. The carrier and reagent can be combined through coating the carrier or combining the carrier and reagent. The treated carriers and urea are encapsulated in a soluble capsule which is administered to a patient. A buffer can be added, if desired, to obtain more specific results. The density of the carriers cause the capsule to descend to the gastric mucosa. The gastric juices dissolve the capsule containing the reagents and urea thereby placing the two reagents and urea combination in direct contact with the gastric mucosa. The urea reacts with any urease present on the mucosa, creating ammonia which causes the pH within the stomach to increase. The two reagents react differently, through color change, to the increase in pH, which is viewed through use of an endoscope. A preferred first reagent is bromothymol blue (dibromothymolsulfonphthalein), which changes yellow in the presence of urease, and a preferred second reagent is phenol red (phenolsulfonphthalein), which turns red in the presence of urease.

DETAILED DESCRIPTION OF THE INVENTION

The instant disclosure uses indicators to detect pH change, as a result of the presence of *H. pylori* in the stomach, during endoscopy. A change in the colors of the indicators reflects the pH change within the stomach; a certain combination indicating a pH reaction to the presence of Helicobacter, or *H. pylori*, organisms.

Urea has the formula $H_2NCONH_2$ and is a naturally occurring product of protein metabolism. Gastric materials from humans or other animals having gastrointestinal disorders contain relatively large quantities of urease (urea aminohydrolase), which hydrolizes urea to ammonium carbonate or ammonia and carbon dioxide. Normally urease is present in the body in only trace amounts, performing the function of decomposing urea. *H. pylori* increases the amount of urease above normal in the affected areas. The increased urease reacts with the administered urea by creating ammonia, which causes an indicator color change due to the increased alkalinity.

The indicators useful in this invention are weak acids with sharply different colors in their dissociated (ionized) and undissociated (neutral) states. The indicators useful herein are medically approved and have $pK_a$ values of from about 6.5 to about 8.5, preferably from about 7.0 to about 8.0. The color exhibited by the indicator in the present composition will depend upon the pH of the composition, the particular indicator used, and the dissociation constant ($K_a$) for that indicator (i.e., $pK_a$ |$log_{10}K_a$). As the color exhibited by the indicator changes over a range of pH values ($pH=log_{10}$ [H+]), the indicators useful in the present compositions change color over a pH range of from about 5.5 to about 9.0, preferably from about 6.5 to about 8.5. The pH of the present compositions are accordingly adjusted to a pH at least about one pH unit lower than the $pK_a$ of the indicator used (i.e. having a hydrogen ion concentration [H+] ten times less than (10% of) the hydrogen ion concentration in a solution having a pH equal to the $pK_a$ of the indicator). Preferably, the pH is adjusted to a pH about two pH units below the $pK_a$ of the indicator. Adjustment of the pH of the present compositions can be effected by addition of a base (e.g. sodium hydroxide) or an acid (e.g. hydrochloric acid or citric acid). Thus, preferably, the pH of the composition of this invention is adjusted to a pH of from about 5.0 to about 6.5, with the preferred embodiment being from about 5.0 to about 6.0.

The preferred reagents are bromothymol blue (dibromothymolsulfonphthalein) indicator, Reagent 1, and phenol red (phenolsulfonphthalein) indicator, Reagent 2. Other indicators useful herein include p-nitrophenol, neutral red (2-methyl-3-amino-6-dimethylaminophenazine), quinoline blue (cyanine), cresol red (o-cresolsulfonphthalein), and thymol blue (thymolsulfonphthalein). The reagents used herein must have a pH indicator range which can reflect the range of pH encountered with the the stomach, generally between 5.5 to 9.0. Indicators approved for medical use and useful herein are described in the The Merk Index (9th ed. 1976), incorporated by reference herein. Reagents are commonly used in conjunction with biopsies, such as disclosed in U.S. Pat. Nos. 4,748,113 to Marshall and 3,873,269 to Kraffczyk, the disclosures of which are incorporated herein as though recited in full. Reagent 2 has urea added to react with the urease enzyme, if present. The urea penetrates the mucus layer of the stomach to come into contact with the urease-containing bacteria, *H. pylori*, on the stomach wall. The urea/urease combination creates ammonia which migrates outward through the mucus layer to come into contact with the Reagents.

The urea is added to a dense carrier, soluble in gastric juices, at approximately 1–20 grams per kilogram of carrier. The preferred carrier is beads, such as nu-pareil beads, although any carrier approved for pharmacological use can be used which has sufficient density to deposit the capsule to the stomach mucosa. The density of the carrier is critical in that it must be able to migrate, or descend to the gastric mucosa, therefore requiring a density, or weight, greater than that of the body fluids. Appropriate dense carriers for use in the medical arts will be readily known to those skilled in the art. It is preferred that the carrier have a neutral pH to prevent interference with the test results. In the event that the carrier has a non-neutral pH, acidic or alkaline ingredients should be incorporated within the capsule to compensate for the carrier's pH.

In the preferred embodiment the Reagents 1 and 2 are put into the stomach in a solid phase, such as beads, which can be individually identified in the stomach. The reagents should be coated onto small diameter beads, preferably 0.2–3.0 mm, with the preferred size being approximately 2 mm. The 2 mm. bead size provides the advantages of visibility as well as preventing obstruction of the endoscope in the event not all of the beads dissolve. A suitable method of making such beads would be to use sugar beads, such as nu-pareil seeds, with a mesh size of 25–35. The nu-pareil beads provide the density required to migrate to the mucosa, either in the capsule or after the capsule dissolves. A less dense vehicle, which floats within the gastric juices, would prevent the Reagents from being placed onto the mucosa.

The choice of the carrier is contrasted with those in the Stern and Brindamour patents wherein the carriers float within the gastric juices. U.S. Pat. No. 3,121,041, issued to Stern et al, discloses the use of a plug, impregnated with a radioactive material, in combination with a soluble capsule. The spongy plug disclosed in Stern would float within the gastric juices, providing several disadvantages. In order to obtain the contrasting results of the two reagents, two impregnated sponges must be used within the capsule, thereby increasing manufacturing expenses. The Stern et al patent discloses tapping the sponges into the capsule. The use of two sponges would possibly double the time required to produce the Stern capsule. Additionally, as the sponges would float within the gastric juices, the Reagents would be diluted and possibly affected by the contents of the gastric juices. The Reagents must be placed directly onto the mucosa to allow the urea to migrate to the stomach wall, react with the urease created by the *H. pylori*, create ammonia, and subsequently alter the pH. To allow for a dilution factor would require increasing the amount of urea used in the capsule. By placing the urea directly onto the mucosa, dilution is reduced to a minimum and therefore a small quantity produces superior accuracy. The beads cannot be coated as commonly known in the time release capsule art, as the reagents on all the beads must be activated simultaneously to obtain a reliable reading. U.S. Pat. No. 3,383,283 to Brindamour discloses time release beads coated with a fatty acid. The fatty acid coating, along with many other coatings, could cause all or some of the beads to float within the gastric juices, again preventing contact with the mucosa.

The disclosed testing procedure is performed in vivo, thereby frequently eliminating the need for a biopsy. In order to view the reagent color change, the beads must remain in a single area. To accomplish this, the beads must not float, but rather lie directly on the mucosa, at the source of the bacteria. It has recently been discovered that *H. pylori* within the stomach is not continuous or in large areas, but rather patchy areas within the stomach wall. In the instant disclosure, the natural dispersal of the beads onto the mucosa covers a sufficient area to react with at least one area of *H. pylori* bacteria. Any floating indicators which come in contact with the mucosa on either a temporary or scattered basis, have a narrow chance to come in direct contact with the affected area and would thus produce unreliable results.

Carriers which do not dissolve after a few minutes in the stomach can cause an obstruction of the endoscope if they are below the preferred size. As stated heretofore, other types of dense, vehicles, approved for pharmacological use, can be used as long as they are capable of absorbing the required reagents, have sufficient density to place the capsule, or its contents, onto the mucosa and dissolving within a few minutes. When using a powdered carrier, the reagents are mixed with the carrier, the carrier is allowed to dry, and, if necessary, re-ground to powder form. The beads have the advantage that coating the beads with the reagents is a simpler, more economical method of obtaining optimum results.

An example of manufacture of the beads would be:

Reagent 1 bromothymol blue indicator buffer (pH=6.0)

sugar beads

Reagent 2 phenol red indicator buffer (pH=6.0)

sugar beads urea

The beads are preferably encapsulated into a quick-dissolving gelatin capsule for delivery to the stomach in mass and undiluted. The capsule can be swallowed with a small amount of liquid, such as water, to more rapidly deliver the capsule and speed the dissolving of the capsule. If necessary, a buffer, such as citrate, having a pH between 4.0 and 6.0 can be added to the liquid to render the gastric pH initially slightly acid. Reagents applied in liquid form will mix with each other, even if taken separately, providing an indefinite result.

Additional ingredients can be added with the reagents to produce any specific desired results. An example of this would be to buffer an Acid pH with a stable buffer such as citrate buffer at pH 6.0, 30 mls. The buffer can be added to the seed-coating along with the reagents or can be placed in powdered form in the capsule. The use of a buffer adds stability to the shelf life of the capsules.

In FIG. 1 the stomach wall, bacteria with urease, and mucus layers are shown with the reagent beads resting on the mucus layer. As the urea released from the Reagent 2 comes in contact with the urease, ammonia is generated. The ammonia rises through the mucus layer and comes into contact with the Reagent indicators, causing an increase in the pH and the Reagents to change color.

In order to reduce false readings, the patient should fast overnight prior to the test. This is well known in the prior art and fasting, as well as other known procedures, should be observed prior to conducting the testing procedure disclosed herein.

To administer the test, the subject takes one to two capsules with 30 mls. of pH 6.0 buffer immediately before endoscopy. It takes approximately 5 minutes for the endoscope to reach the stomach, at which time the capsules have dissolved and the granules are resting and slowly dissolving on the surface of the gastric mucosa. Through the endoscope, the examining person can detect the color changes of the reagents, if any, which indicate the presence of the Helicobacter organisms.

In the following example Reagent 2 is yellow at acid pH, changing to red at alkaline pH and Reagent 1 is yellow at acid pH, changing to blue at alkaline pH. The instant invention relies on a differential color change to identify a true positive from a false positive reaction. It is the differential which is of importance, not the colors themselves and any colors and/or reagents specifically used herein are examples and in no way limit the scope of the invention.

| READING EXAMPLE I Negative result, (no urease, stomach is acid) | | |
|---|---|---|
| Reagent 1 (yellow) | | Both remain yellow |
| | no urease | |
| Reagent 2 (yellow) | | no pH change occurs |
| READING EXAMPLE II False positive result (stomach has an alkaline pH; for example, bile is in stomach or patient salivates excessively) | | |
| Reagent 1 (yellow) | | Changes to blue |
| | no urease, pH > 6.5 | |
| Reagent 2 (yellow) | | Changes to red |
| READING EXAMPLE III True positive result (stomach is acid but contains urease) | | |
| Reagent 1 (yellow) pH < 6 | urease | Remains yellow no pH change occurs. |
| Reagent 2 (yellow) | urease | Changes red pH rises > 6.5 |

The presence of red and yellow reagent, but not blue reagent, indicates that urease is in the stomach (i.e. Helicobacter).

A false positive is produced by means of the first indicator indicating an alkaline environment without the influence of the ammonia generated by the urea-urease reaction.

The positive indication is produce by the first indicator showing the presence of an acid environment and the second indicator showing the presence of an alkaline environment. The difference in the reactions to the same environment is due to the presence of the urea in the second indicator. Unlike the first indicator, the second indicator interacts with urease which is present, to generate ammonia.

Thus, where each of the two indicators respond to an acid environment, urease is not present and therefore Helicobacter is not present, since urease would be present if Helicobacter were present.

The negative result is simply due to neither indicator indicating an alkaline condition and consequently indicating an absence of urease generated by Helicobacter.

The unique aspect of the invention is the use of the reagent which is capable of reacting with urease to produce a product which can be readily detected. Urea reacts with urease to release ammonia, which can be detected by pH indicators. Indicators which undergo color changes are well known in the art are commonly used, and can readily be observed though endoscopy.

If the urea were not used, an alkaline environment in the stomach could be mistaken for the presence of Helicobacter.

What is claimed is:

1. A method of detecting, in vivo, a presence or absence of urease producing Helicobacter in a patient's stomach comprising the steps of:
   (a) administering to a patient a pharmaceutically acceptable soluble container containing a combination comprising:
      said first indicator having a pH indicium range of from about 5.5 to about 9.0 and having
         a first indicium for indicating an acidic pH range and
         a second indicium for indicating an alkaline pH range, and
      a second indicator combination, said second indicator combination having
         a second pH indicator having a pH indicium range of from about 5.5 to about 9.0 and having
         a second pH indicator first indicium for indicating an acidic pH range and
         a second pH indicator third indicium for indicating an alkaline pH range, and
      a reagent to react with urease in said stomach to form an alkaline product,
         said first pH indicator first indicium and said second pH second indicator first indicium being the same,
         said first pH indicator second indicium and said second pH indicator combination third indicium being different from one another, from said first pH indicator first indicium and from said second pH indicator first indicium,
   (b) dissolving said soluble container in said patient's stomach fluids,
   (c) contacting said patient's gastric mucosa with said first pH indicator and said second indicator combination,
   (d) observing said first pH indicator and said second indicator combination in the patient's stomach, wherein if:
      (1) said first pH indicator first indicium and said second indicator combination first indicium indicate an acidic pH range, then said stomach is acidic thereby indicating an absence of urease producing Helicobacter;
      (2) said first pH indicator second indicium and said second indicator combination third indicium indicate an alkaline pH range, then said stomach is alkaline whereby no determination can be made regarding the presence or absence of urease producing Helicobacter; or
      (3) said first pH indicator first indicium indicates an acidic pH range and said second indicator combination third indicium indicates an alkaline pH range, then said stomach is acidic indicating the presence of urease producing Helicobacter.

2. The method of claim 1 wherein both said first indicator and said second indicator combination are carried by a pharmaceutically acceptable dense carrier having a density greater than body fluids, said pharmaceutically acceptable dense carrier delivering said first indicator and said second indicator combination to the gastric mucosa.

3. The method of claim 2 wherein said dense carrier is dissolved in said gastric fluids after said soluble container is dissolved.

4. The method of claim 2 wherein said pharmaceutically acceptable carrier is sugar beads.

5. The method of claim 2 wherein said carrier has a diameter from about 0.2 to about 3.0 mm, thereby facilitating dispersal of said indicators over said gastric mucosa.

6. The method of claim 2 wherein a first portion of said carrier is coated with said first indicator and a second portion of said carrier is coated with said second indicator combination.

7. The method of claim 2, wherein said first indicator is sorbed by a first portion of said carrier and said second indicator combination is sorbed by a second portion of said carrier.

8. The method of claim 2 wherein a buffer is added to said dense carrier in order to neutralize the pH of said dense carrier.

9. The method of claim 1 wherein said reagent is urea, said urea reacting with said urease produced by Helicobacter to generate ammonia.

10. The method of claim 1 wherein said first pH indicator and said second pH indicator are weak acids that exhibit a first color that indicates an acid pH range and a second color that indicates an alkaline range.

11. The method of claim 1 wherein said first pH indicator is bromothymol blue (dibromothymolsulfonphthalein) and said second pH indicator is phenol red (phenolsulfonphthalein).

12. A method for diagnosis of gastrointestinal disorders caused by urease producing Helicobacter by determining the presence or absence of urease within a subject's stomach comprising the steps of:
   (a) administering to said subject between approximately 1 and 20 grams of urea per kilogram of dense, pharmaceutically acceptable carrier, said carrier having a density greater than body fluids, said urea being carried by said dense carrier, a first portion of said dense carrier being in combination with a pharmaceutically acceptable first pH indicator having range of from about 5.5 to about 9.0 and having a first indicium at an acidic pH range and a second indicium at an alkaline pH range, and a second portion of said dense carrier being in combination with a pharmaceutically acceptable second pH indicator having range of from about 5.5 to about 9.0, and having a first indicium at an acidic pH range and a third indicium at an alkaline pH range, said carrier, said pH indicators and said urea being encapsulated in a capsule, said capsule being soluble in gastrointestinal fluids, said first pH indicator first indicium and said second pH second indictor first indicium being the same, said first pH indicator second indicium and said second pH indicator combination third indicium being different from one another and from said first pH indicator first indicium and said second pH indicator first indicium,
   (b) drinking a predetermined quantity of a liquid, delivering said capsule through stomach fluids to said subject's gastric mucosa, said dense carrier causing said first pH indicator, said second pH indicator and said urea to descend through said stomach fluids, (c) dissolving said capsule in gastric juices contained in said subject's stomach, thereby placing said carrier, said pH indicators and said urea in direct contact with said gastric mucosa, (d) reacting said urea with any urease present to produce ammonia, thereby raising the pH proximate said indicators within the subject's stomach, (e) viewing said first pH indicator indicium and said second pH indicator indicium for an indication of pH change, said pH change indicating the absence or presence of Helicobacter;

wherein when viewed if:

1—said first indicium of said first pH indicator and said first indicium of said second pH indicator are a color that indicate an acidic range, then there is an absence of urease and a negative indication of the presence of said Helicobacter;

2—said second indicium of said first pH indicator and said third indicium of said second pH indicator are a color which indicate an alkaline pH range, then no determination regarding a gastrointestinal disorder can be made; or 3—said first indicium of said first pH indicator is a color that indicates an acidic range and said third indicium of said second pH indicator is a color that indicates urea in said second pH indicator combination is reacting with said urease to create an alkaline pH, then there is a positive indication of a presence of Helicobacter, thereby indicating a Helicobacter caused gastrointestinal disorder.

13. The method of claim 12 further comprising the step of administrating an acidic fluid to said subject prior to administering said capsule, thereby eliminating false positive readings.

14. A method of in vivo detection of urease producing Helicobacter in a patient's stomach, comprising the steps of:

a. providing at least two separate groups of pharmaceutically acceptable pH indicator sorbing dense carriers having a density greater than body fluids to cause said carriers to descend through the patient's gastric fluids to said patient's gastric mucosa;

b. combining a first of said at least two separate groups of dense carriers with a pharmaceutically acceptable first pH indicator that exhibits a first indicium when exposed to an acidic pH range and a second indicium when exposed to an alkaline pH range;

c. combining a second of said at least two separate groups of dense carriers with a combination of a pharmaceutically acceptable second pH indicator and urea, said second pH indicator exhibiting a first indicium when exposed to an acidic pH range and a third indicium when exposed to an alkaline pH range, said first pH indicator first indicium and said second pH second indictor first indicium being the same, said first pH indicator second indicium and said second pH indicator combination third indicium being different from one another and from said first pH indicator first indicium and said second pH indicator first indicium;

d. administering said first dense carrier and said second dense carrier to a patient;

e. contacting said patient's gastric mucosa with said first indicator, said second indicator and said urea contained within said carriers;

f. raising pH levels proximate said second pH indicator and urea in response to the increased ammonia generated by a reaction between said urea and said urease;

g. observing the indication of urease producing Helicobacter in said patient's stomach by observing said first pH indicator and said second pH indicator combination, wherein:

(1) both said first indicium of said first indicator and said first indica of said second indicator combination indicating an acidic pH range indicates an absence of Helicobacter and that said stomach is acidic;

(2) both said second indicium of said first indicator and said second indicium of said second indicator combination indicating a false positive result and that said stomach is alkaline; or (3) said second indicium of said first indicator indicating an acidic pH range and said second indicium of said second indicator combination indicating an alkaline pH range, signifies the presence of urease producing Helicobacter and that said stomach is acidic;

h. determining, based on observation 1, that the stomach is acidic and that there is an absence of urease producing Helicobacter; observation 2, that the stomach is alkaline and no determination can be made; or observation 3, that there is a presence of urease producing Helicobacter in said patient's stomach.

15. A method of in vivo detection of urease producing Helicobacter in a patient's stomach, comprising the steps of:

a. providing at least two separate groups of pharmaceutically acceptable pH indicator sorbing dense carriers having a density greater than body fluids to cause said carriers to descend through the patient's gastric fluids to the patient's gastric mucosa;

b. combining a first of said at least two separate groups of dense carriers with a pharmaceutically acceptable first pH indicator which exhibits a first indicium when exposed to an acidic pH range and a second indicium when exposed to an alkaline pH range;

c. combining a second of said at least two separate groups of dense carriers with a combination of a pharmaceutically acceptable second pH indicator and urea, said second pH indicator exhibiting a first indicium when exposed to an acidic pH range and a third indicium when exposed to an alkaline pH range, said first pH indicator first indicium and said second pH second indictor first indicium being the same, said first pH indicator second indicium and said second pH indicator combination third indicium being different from one another and from aid first pH indicator first indicium and said second pH indicator first indicium;

d. administering said first dense carrier and said second dense carrier to a patient;

e. contacting the patient's gastric mucosa with said first indicator contained within said first dense carrier and said second indicator and said urea contained within said second dense carrier;

f. observing said first pH indicator and said second pH indicator combination to determine if pH levels in the patient's stomach are raised proximate said second pH indicator and urea as a response to an increase in ammonia generated by a reaction between said urea and said urease produced by said Helicobacter, wherein:

(1) both said first indicium of said first indicator and said first indicium of said second pH indicator and urea indicating an acidic pH range indicates an absence of Helicobacter, that said stomach is acidic and there is an absence of urease producing Helicobacter;
(2) both said second indicium of said first indicator and said second indicium of said second pH indicator and urea indicates an alkaline pH range indicating that said stomach is alkaline and that no determination can be made as to the absence or presence of urease producing Helicobacter thereby indicating a false positive result; or
(3) said second indicium of said first pH indicator indicating an acidic pH range and said second indicium of said second pH indicator and urea indicating an alkaline pH range, indicates the presence of urease producing Helicobacter and that said stomach is acidic.

* * * * *